United States Patent [19]
Rosen et al.

[11] Patent Number: 5,663,349
[45] Date of Patent: Sep. 2, 1997

[54] PREPARATION OF SUBSTITUTED PIPERIDENES

[75] Inventors: Terry J. Rosen, East Lyme; Dennis M. Godek, Glastonbury; Sally Gut, Madison; Lewin Wint, Uncasville, all of Conn.

[73] Assignee: Pfizer Inc., New York, N.Y.

[21] Appl. No.: 273,662

[22] Filed: Jul. 12, 1994

Related U.S. Application Data

[63] Continuation of Ser. No. 800,667, Nov. 27, 1991, Pat. No. 5,364,943, which is a continuation-in-part of Ser. No. 531,265, filed as PCT/US91/02541, Apr. 12, 1991, published as WO91/018878, Dec. 12, 1991, abandoned.

[51] Int. Cl.$^6$ ............... C07D 215/12; C07D 215/04; C07D 211/02; C07D 211/68
[52] U.S. Cl. ............... 546/174; 546/176; 546/185; 546/193; 546/207; 546/208; 546/212; 546/214; 546/264
[58] Field of Search ............... 546/185, 174, 546/176, 193, 207, 208, 212, 214, 264

[56] References Cited

U.S. PATENT DOCUMENTS

| | | |
|---|---|---|
| 3,560,510 | 2/1971 | Warawa et al. . |
| 4,358,446 | 11/1982 | Haken et al. . |
| 4,377,691 | 3/1983 | Yasui et al. ............... 546/185 |
| 4,552,960 | 11/1985 | Krumkalns et al. . |
| 4,680,283 | 7/1987 | Veber et al. . |
| 5,138,060 | 8/1992 | Godek et al. . |
| 5,162,339 | 11/1992 | Lowe . |

FOREIGN PATENT DOCUMENTS

| | | |
|---|---|---|
| A10015628 | 9/1980 | European Pat. Off. . |
| A20100158 | 2/1984 | European Pat. Off. . |
| 0129433 | 12/1984 | European Pat. Off. . |
| 2056974 | 3/1981 | United Kingdom . |
| 9109844 | 7/1991 | WIPO . |
| WO92/12151 | 7/1992 | WIPO . |
| WO92/17449 | 10/1992 | WIPO . |
| WO93/00331 | 1/1993 | WIPO . |
| WO93/00330 | 1/1993 | WIPO . |

OTHER PUBLICATIONS

Chem. Abs., 91:140686 (1979), Rakhit et al.
Solomons et al., Organic Chemistry (1976).
E. J. Warawa et al. "Quinuclidine Chemistry", J. Med. Chem., 18, 587 (1975).
Sandberg et al. "Substance P," J. Med. Chem., 25, 1009, (1982).
P.J. Goadsby et al. "Release of Vasoactive Peptides" Ann. Neurol., 23, 193 (1988).
Regoli, "Neurokinin Agonists & Antagonists" Elsevier Scientific Publishers, Amsterdam, pp. 85–95 (1987).
L.S. Trifonov et al. "Synthesis of 1,2–Five–Ring–Annellated Barrelenes" Helvetica Chimica Acta, 70, 4, 1732–1736 (1987).
A.S. Yanni et al., "Synthesis & biological Activity" Indian J. Chem., 21B (7), 705–6, (1982).
Y.P. Gupta et al. "Synthesis of 2,12–Diazachrysene via Benzyne Cyclization Reaction," Indian J. Chem., 19B (5), 400–1, (1980).
V.N. Gogte et al. "Infrated Spectral Study of the Effect of Substitution on Conformation and Hydrogen Bonding in 3–(aryl–amino)propanols," Indian J. Chem., 17B (3), 230–2, (1979).
S.V. Kessar et al. "New Routes to Condensed Polynuclear Compounds," Tetrahedron, 29, Pergamon Press, (GB), 419–424, 1978.
G.N. Walker et al. "Synthesis of Caried Heterocyclic & Substituted Arylalkyl" J. Med. Chem., 9, No. 4, (1966), 624–630.
G.N. Walker et al. "Application of Sodium Borohydride" Journal of Organic Chemistry, 26, No. 8, (1961), American Chemical Society, (US), 2740–2747.
Suman Rakhit et al. "Formation of Animals from Amines via Pummerer Rearrangement," Can. J. Chem., 57, No. 10, 1153 (1979).
Webster's Ninth New Collegiate Dictionary, p. 745 (1990).
Morrison et al., *Organic Chemistry*, pp. 92–93, (3rd Ed., Allyn and Bacon, Inc.) (1973).
Greene et al., *Protective Groups in Organic Synthesis*, pp. 1–9, 309–317, 349, 350, 362, 363 and 372, (2nd Ed., John Wiley & Sons, Inc.) (1991).

*Primary Examiner*—C. H. Kelly
*Attorney, Agent, or Firm*—Peter C. Richardson; Paul H. Ginsburg; Garth C. Butterfield

[57] ABSTRACT

Novel processes are disclosed for the preparation and resolution of substituted piperidines of the formula

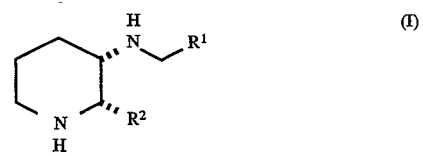

(I)

wherein $R^1$ and $R^2$ are defined as below, and related compounds, as well as novel intermediates used in such processes.

48 Claims, No Drawings

PREPARATION OF SUBSTITUTED PIPERIDENES

BACKGROUND OF THE INVENTION

This is a continuation of application Ser. No. 07/800,667, filed on Nov. 27, 1991, now U.S. Pat. No. 5,364,943 continuation-in-part of PCT application Ser. No. 91/02541 filed on Apr. 12, 1991, which was published as WO 91/18, 878 on Dec. 12, 1991 and a continuation-in-part of U.S. application No. 07/531,265 filed May 31, 1990 abandoned.

This invention to novel processes for the preparation and resolution of substituted intermediates used in related compounds, as well as to novel intermediates used in such processes.

The substituted piperidines and related compounds that can be prepared by the processes of this invention are substance P receptor antagonists and are therefore useful in treating diseases mediated by an excess of substance P.

Substance P is a naturally occurring undecapeptide belonging to the tachykinin family of peptides, the latter being named for their prompt stimulatory action on smooth muscle tissue. More specifically, substance P is a pharmacologically-active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has been shown to be involved in the transmission of pain or migraine [see B. E. B. Sandberg et al., *Journal of Medicinal Chemistry*, Vol. 25, p. 1009 (1982)], as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract, such as ulcerative colitis and Crohn's disease, etc. (see D. Regoli in "Trends in Cluster Headache," Edited by F. Sicuteri et al., Elsevier Scientific Publishers, Amsterdam, 1987, pp. 85–95).

The substituted piperidines and related compounds that can be prepared by the methods of this invention are claimed in PCT patent application PCT/US 90/00116, filed Jan. 4, 1990, and assigned in common with the present application.

SUMMARY OF THE INVENTION

The present invention relates to a process for preparing compounds of the formula

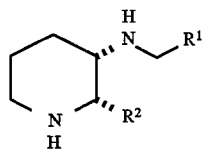

wherein $R^1$ is aryl selected from indanyl, phenyl and naphthyl; heteroaryl selected from thienyl, furyl, pyridyl and quinolyl; and cycloalkyl having 3–7 carbon atoms, wherein one of said carbon atoms may optionally be replaced by nitrogen, oxygen or sulfur; wherein each of said aryl and heteroaryl groups may optionally be substituted with one or more substituents, and said ($C_3$–$C_7$) cycloalkyl may optionally be substituted with one or two substituents, said substituents being independently selected from halo, nitro, amino, cyano, phenyl, hydroxyl, ($C_1$–$C_6$)alkylamino,

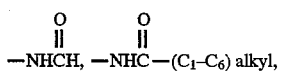

($C_1$–$C_{10}$) alkoxy optionally substituted with from one to three flourine atoms and ($C_1$–$C_{10}$) alkyl optionally substituted with from one to three fluorine atoms, wherein the nitrogen atoms of said amino, and ($C_1$–$C_6$)alkylamino groups may optionally be protected with an appropriate protecting group; and $R^2$ is thienyl, benzhydryl, naphthyl or phenyl optionally substituted with from one to three substituents independently selected from chloro, bromo, fluoro, iodo, ($C_1$–$C_{10}$) alkoxy optionally substituted with from one to three flourine atoms and ($C_1$–$C_{10}$) alkyl optionally substituted with from one to three fluorine atoms, comprising:

(a) reacting a compound of the formula

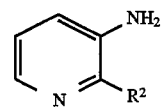

wherein $R^2$ is defined as above, with either (i) a compound of the formula

wherein $R^1$ is defined as above and X is a leaving group (e.g., chloro, bromo, iodo or imidazole), followed by treatment of the resulting amide with a reducing agent, (ii) a compound of the formula $R^1CHO$, wherein $R^1$ is defined as above, in the presence of a reducing agent, or (iii) a compound of the formula $R^1CH_2X$, wherein $R^1$ is defined as above and X is a leaving group (e.g., chloro, bromo, iodo, mesylate or tosylate), to produce a compound of the formula

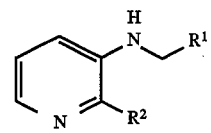

wherein $R^1$ and $R^2$ are defined as above; and (b) reducing the compound of formula II so formed.

The compounds of formula I have chiral centers and therefore exist in different enantiomeric forms. Formula I, as depicted above, includes all optical isomers of such compounds, and mixtures thereof.

The present invention also relates to a process for preparing compounds of the formula I, as depicted above, wherein $R^1$ and $R^2$ are defined as above, comprising reacting a compound of the formula IV, as depicted above, wherein $R^2$ is defined as above, with a compound of the formula $R^1CHO$, wherein R is defined above, in the presence of a drying agent or using an apparatus designed to remove azeotropically the water generated, to produce an imine of the formula

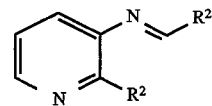

wherein $R^1$ and $R^2$ are defined as above, and then either reducing the imine with hydrogen to form directly a compound of the formula I, or reacting the imine with a reducing agent to form a compound of the formula II, as depicted above, wherein $R^1$ and $R^2$ are defined as above, and then reacting the compound of formula II with a reducing agent to form a compound of the formula I.

The present invention also relates to a process for preparing compounds of the formula II, as depicted above, wherein $R^1$ is defined as above, comprising: (a) reacting a compound of the formula

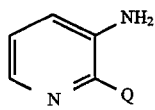   (V)

wherein Q is hydrogen, chloro, fluoro, bromo or iodo, with either (i) a compound of the formula

$R^1CX$, wherein $R^1$ is defined as above and X is a leaving group (e.g., chloro, bromo, iodo or imidazole), followed by treatment of the resulting amide with a reducing agent, (ii) a compound of the formula $R^1CHO$, wherein $R^1$ is defined as above, in the presence of a reducing agent, or (iii) a compound of the formula $R^1CH_2X$, wherein $R^1$ is defined as above and X is a leaving group (e.g., chloro, bromo, iodo, mesylate or tosylate), to produce a compound of the formula

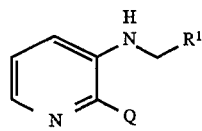   (III)

wherein $R^1$ and Q are defined as above; and (b) reacting the compound of formula III so formed with $(R^2)$-halogen, wherein $R^2$ is defined as above and halogen represents chlorine, fluorine, bromine or iodine, in the presence of a transition metal catalyst, or with an $R^2$-containing organometallic compound such as $(R^2)$-magnesium halide or $(R^2)$-lithium, wherein $R^2$ is defined as above and halide represents chloride, fluoride, bromide or iodide.

The present invention also relates to a process for converting compounds of the formula V, as depicted above, wherein Q is defined as above, into compounds of the formula II, as depicted above, wherein $R^1$ is defined as above, comprising: (a) adding —$CH_2R^1$, wherein $R^1$ is defined as above, to the amino group by reaction with either (i) a compound of the formula

$R^1CX$, wherein $R^1$ is defined as above and X is a leaving group (e.g., chloro, bromo, iodo or imidazole), followed by treatment of the resulting amide with a reducing agent, (ii) a compound of the formula $R^1CHO$, wherein $R^1$ is defined as above, in the presence of a reducing agent, or (iii) a compound of the formula $R^1CH_2X$, wherein $R^1$ is defined as above and X is a leaving group (e.g., chloro, bromo, iodo, mesylate or tosylate); and (b) displacing Q with $R^2$ by reaction with an $R^2$ containing organometallic compound such as $(R^2)$-magnesium bromide or $(R^2)$-lithium, or with $(R^2)$-halogen, wherein halogen represents chlorine, fluorine, bromine or iodine; or performing the foregoing reaction steps (a) and (b) in the opposite order.

The present invention also relates to a process for preparing compounds of the formula I, as depicted above, wherein $R^1$ and $R^1$ are defined as above, comprising reacting a compound of the formula III, as depicted above, wherein $R^1$ and Q are defined as above, with $R^2$-halogen, wherein $R^2$ is defined as above and halogen represents chlorine, fluorine, bromine or iodine, in the presence of a transition metal catalyst, or with an $R^2$-containing organometallic compound such as $(R^2)$-magnesium bromide, or $(R^2)$-lithium, wherein $R^2$ is defined as above, to produce a compound of the formula II, as depicted above, wherein $R^1$ and $R^2$ are defined as above, and then reducing the compound of formula II so formed.

The present invention also relates to a process for preparing the enantiomer of a compound of the formula I having the absolute stereochemistry depicted above for formula I, wherein $R^1$ is 2-methoxyphenyl and $R^2$ is phenyl, comprising reacting a racemic mixture of such compound with (R)-(–)-mandelic acid in a suitable organic reaction inert solvent, removing the solvent by filtration, and treating the resulting salt with a suitable base.

The present invention also relates to a process for preparing the enantiomer of a compound of the formula I having the absolute stereochemistry depicted above for formula I, wherein $R^1$ is 5-trifluoromethoxy-2-methoxyphenyl and $R^2$ is phenyl, comprising reacting a racemic mixture of such compound with (S)-(+)-mandelic acid in a suitable reaction inert solvent, removing the solvent by filtration, and treating the resulting salt with a suitable base.

The present invention also relates to compounds having the formula

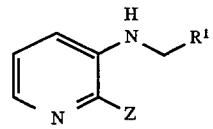

wherein $R^1$ is defined as above, and Z is $R^2$ or Q wherein $R^2$ and Q are defined as above.

DETAILED DESCRIPTION OF THE INVENTION

The processes and products of the present invention are illustrated in the following reaction scheme. Except where otherwise indicated, in the reaction scheme and discussion that follow, formulas I, II, III, IV, and V, and substituents $R^2$, $R^2$, $R^3$, Q, X and halogen are defined as above.

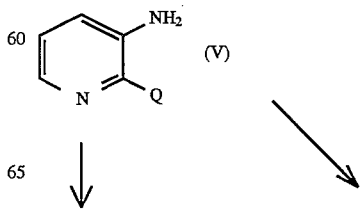

-continued

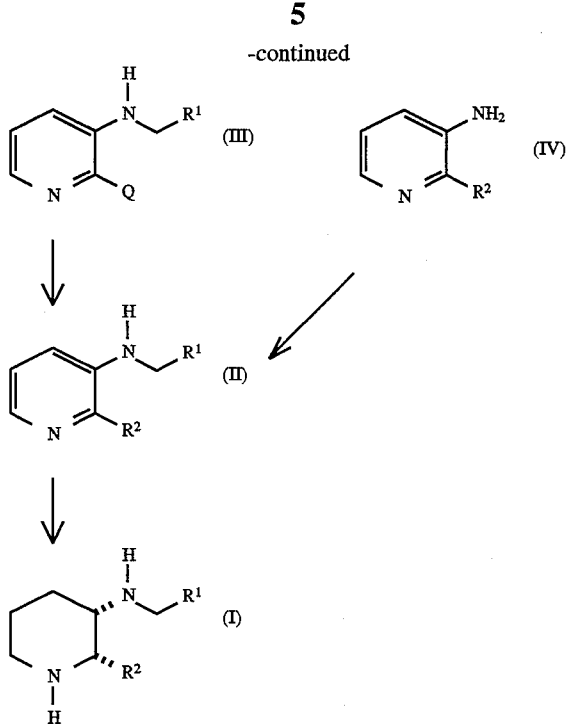

The reaction of a compound of the formula IV with a compound of the formula R¹CHO to produce a compound of the formula II is typically carried out in the presence of a reducing agent such as sodium cyanoborohydride, sodium triacetoxyborohydride, sodium borohydride, hydrogen and a metal catalyst, zinc and hydrochloric acid, or formic acid at a temperature from about −60° C. to about 50° C. Suitable reaction inert solvents for this reaction include lower alcohols (e.g., methanol, ethanol and isopropanol), acetic acid and tetrahydrofuran (THF). Preferably, the solvent is acetic acid the temperature is about 25° C., and the reducing agent is sodium triacetoxyborohydride.

Alternatively, the reaction of a compound of the formula IV with a compound of the formula R¹CHO may be carried out in the presence of a drying agent or using an apparatus designed to remove azeotropically the water generated, to produce an imine of the formula

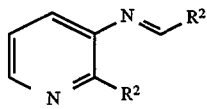

which is then reacted with a reducing agent as described above, preferably with sodium triacetoxyborohydride at about room temperature. The preparation of the imine is generally carried out in a reaction inert solvent such as benzene, xylene or toluene, preferably toluene, at a temperature from about 25° C. to about 110° C., preferably at about the reflux temperature of the solvent. Suitable drying agents/solvent systems include titanium tetrachloride/dichloromethane and molecular sieves/THF. Titanium tetrachloride/dichloromethane is preferred.

The reaction of a compound of the formula IV with a compound of the formula R¹CH₂X is typically carried out in a reaction inert solvent such as dichloromethane or THF, preferably dichloromethane, at a temperature from about 0° C. to about 60° C., preferably at about 25° C.

The reaction of a compound of the formula IV with a compound of the formula $$R^1CX$$
$$\parallel$$
$$O$$

is typically carried out in an inert solvent such as tetrahydrofuran (THF) or dichloromethane at a temperature from about −20° C. to about 60° C., preferably in dichloromethane at about 25° C. Reduction of the resulting amide is accomplished by treatment with a reducing agent such as borane dimethylsulfide complex, lithium aluminum hydride or diisobutylaluminum hydride in an inert solvent such as ethyl ether or THF. The reaction temperature may range from about 0° C. to about the reflux temperature of the solvent. Preferably, the reduction is accomplished using borane dimethylsulfide complex in THF at about 60° C.

Reduction of the pyridine of formula II to form the corresponding piperidine of formula I is generally accomplished using either sodium in alcohol, lithium aluminum hydride/aluminum trichloride, electrolytic reduction or hydrogen in the presence of a metal catalyst. The reduction with sodium is generally conducted in a boiling alcohol, preferably butanol, at a temperature from about 20° C. to about the reflux temperature of the solvent, preferably at about 120° C. The reduction with lithium aluminum hydride/aluminum trichloride is usually carried out in ether, THF or dimethoxyethane, preferably ether, at a temperature from about 25° C. to about 100° C., preferably at about room temperature. The electrolytic reduction is conducted, preferably, at room temperature, but temperatures from about 10° C. to about 60° C. are also suitable.

Hydrogenation in the presence of a metal catalyst is the preferred method of reduction. Suitable hydrogenation catalysts include palladium, platinum, nickel and rhodium. The preferred catalyst for hydrogenation is platinum on carbon. The reaction temperature may range from about 10° C. to about 50° C., with about 25° C. being preferred. The hydrogenation is generally carried out at a pressure from about 1.5 to about 4 atmospheres, preferably at about 3.0 atmospheres.

The reaction of a compound of the formula V with a compound of the formula R¹CHO to form a compound of the formula III is typically conducted in the presence of a reducing agent such as sodium cyanoborohydride, sodium triacetoxyborohydride, hydrogen and a metal catalyst, zinc and hydrochloric acid, or formic acid, at a temperature from about −60° C. to about 50° C. Suitable reaction inert solvents for this reaction include lower alcohols (e.g., methanol, ethanol and isopropanol), acetic acid and tetrahydrofuran. The preferred solvent is acetic acid and the preferred temperature is about 25° C. Sodium triacetoxyborohydride is the preferred reducing agent.

The preparation of compounds of the formula II from the corresponding compounds of the formula III is accomplished, as indicated above, by reacting the appropriate compound of the formula III with (R²)-halogen in the presence of a transition metal catalyst, or with an R²-containing organometallic compound. The transition metal catalyst is optional in reactions utilizing an R²-containing organometallic compound. Examples of suitable R²-containing organic compounds are (R²)-magnesium bromide and (R²)-lithium. This reaction is typically carried out in a reaction inert solvent in the presence of a catalyst such as nickel, copper or palladium and at a temperature from about 0° C. to about 60° C., preferably at about 25° C. Examples of reaction inert solvents that may be used are THF, ether, and toluene. A preferred solvent is THF and a preferred catalyst is [1,2-bis-(diphenylphosphino)ethane] nickel (II) chloride.

The resolution of a racemic mixture of a compound of the formula I wherein $R^1$ is 2-methoxyphenyl and $R^2$ is phenyl to prepare the (+) enantiomer of such compound is generally carried out using methanol, ethanol, or isopropanol, preferably isopropanol, as the organic reaction inert solvent. Preferably, the resolution is carried out by combining a racemic mixture of a compound of the formula I and (R)-(−)-mandelic acid in isopropanol, and stirring the mixture to form an optically enriched mandelic acid salt precipitate. The optically enriched precipitate is then recrystallized twice from isopropanol, after which the recrystallized precipitate is converted to the free base of the optically pure compound of formula I by partitioning it between dichloromethane and an aqueous base such as sodium hydroxide, sodium bicarbonate or potassium bicarbonate, preferably sodium hydroxide, or by stirring an alcoholic solution of the salt with a basic ion exchange resin. The free base, which is dissolved in the methylene chloride, can then be converted to the corresponding hydrochloric acid salt. Isolation of the mandelate may be conducted at temperatures from about 0° C. to about 40° C. About 25° C. is preferred.

The resolution of a racemic mixture of a compound of the formula I wherein $R^1$ is 5-trifluoromethoxy-2-methoxyphenyl and $R^2$ is phenyl to prepare the (+) enantiomer of such compound is generally carried out using methanol, ethanol, isopropanol, dichloromethane, chloroform, carbon tetrachloride or isopropyl ether preferably isopropyl ether, as the organic reaction inert solvent. Preferably, the resolution is carried out by combining a racemic mixture of a compound of the formula I and (S)-(+)-mandelic acid in isopropyl ether and stirring the mixture to form an optically enriched mandelic acid salt precipitate. The optically enriched precipitate is then preferably recrystallized twice from isopropyl ether, after which the recrystallized precipitate is converted to the free base of the optically pure compound of formula I by partitioning it between dichloromethane and an aqueous base such as sodium hydroxide, sodium bicarbonate or potassium bicarbonate, preferably sodium hydroxide, or by stirring an alcoholic solution of the salt with a basic ion exchange resin. The free base, which is dissolved in the methylene chloride, can then be converted to the corresponding hydrochloric acid salt. Isolation of the mandelate may be conducted at temperatures from about 0° C. to about 40° C. About 25° C. is preferred.

Compounds of the formula I may be prepared and isolated as hydrochloride salts, converted back to the free base form, and then resolved as described above by mixing with (R)-(−)-mandelic acid. This procedure is exemplified in Examples 1C and 4. Alternatively, compounds of the formula I may be prepared by reduction of the corresponding compounds of formula II, as described above, and directly resolved as described above by mixing with (R)-(−)-mandelic acid. This procedure is exemplified in Example 8.

The oxidation of compounds of the formula I to form the corresponding compounds of the formula II is generally carried out using palladium on charcoal, platinum or nickel as the oxidizing agent and xylene, benzene or toluene as the solvent. Palladium on charcoal and xylene are preferred. This reaction may be conducted at temperatures from about 50° C. to about 150° C., preferably at about 100° C.

In each of the reactions discussed or illustrated above, pressure is not critical unless otherwise indicated. Pressures from about 0.5 atmospheres to about 5.0 atmospheres are generally acceptable, and ambient pressure, i.e. about one atmosphere, is preferred as a matter of convenience.

The following examples illustrate the methods and compounds of the present invention but do not limit its scope.

EXAMPLE 1

Cis-3-(2-methoxybenzylamino)-2-phenylpiperidine

A. 2-Chloro-3-(2-methoxybenzylamino)pyridine

To a 5 L 3-necked round bottom flask fitted with mechanical stirrer, thermometer, addition funnel, and nitrogen inlet, were added 1.6 L of acetic acid and 80.0 grams (0.62 moles) of 3-amino-2-chloropyridine. The mixture was agitated for approx. 10 minutes at 25° C. for dissolution. To the resulting solution was charged 105.9 grams (119.3 mL/0.78 moles/ 1.25 equivalents) of o-anisaldehyde (2-methoxybenzaldehyde), upon which was obtained a yellow solution after stirring 10 minutes at 25° C. Over a 30 minute period in portions were added 263.7 grams (1.24 moles, 2.0 equivalents) sodium triacetoxyborohydride, while maintaining a temperature of 20° C. The mixture was stirred for 12–18 hours and concentrated to a semi-solid, which was partitioned between methylene chloride and water (800 mL each). The pH was adjusted to 9.5 with 700 mL 25% sodium hydroxide solution while maintaining a temperature of 25°–30° C. by cooling. The layers were separated, the aqueous layer was washed with methylene chloride (3×300 mL each), and the methylene chloride layers were combined. The organic layer was washed with 300 mL of saturated sodium chloride solution, and then dried with magnesium sulfate for 30 minutes. The magnesium sulfate was removed by filtration, and the methylene chloride filtrate was evaporated and displaced with ethyl acetate, leaving an off white tacky material (174 grams). The product was reslurried in 120 mL of fresh ethyl acetate at 0°–5° C. for 1.5 hours, filtered, washed with cold ethyl acetate and dried, giving 133.2 grams (86.1%) of the title compound. M.P. 121°–125° C. $^1$H NMR (CDCl$_3$) δ 7.70 (dd, 1H, J=1 Hz, 2 Hz), 7.25 (m, 2H), 7.05 (m, 1H), 6.90 (m, 3H), 4.95 (t, 1H), 4.40 (d, 2H, J=6), 3.85 (s, 3H).

B. 3-(2-Methoxybenzylamino)-2-phenylpyridine

To a 22 L three neck round bottom flask equipped with a mechanical stirrer, thermometer, addition funnel, and nitrogen inlet, were added 3.84 L of tetrahydrofuran, 91.6 grams (0.17 moles) of bis(diphenylphosphino)ethanenickel (II) chloride, and 96 grams (0.39 moles) of 2-chloro-3-(2-methoxybenzylamino)pyridine. The orange slurry was stirred at 25° C. for about 30 minutes. Phenylmagnesium bromide (3M in ether, 231.6 mL, 0.69 moles) was added over a 4 hour period and the resulting black slurry was stirred for 22 hours at 25° C. During this time, the reaction was monitored by thin layer chromatography assay, and a total of 86 mL (0.26 moles) of additional phenylmagnesium bromide solution was added to the system. The reaction mixture was cooled to 10° C. and the reaction was quenched with 3.84 L of 20% aqueous HCl over 30 minutes. Ethyl acetate (3.84 L) was added and the reaction mixture was stirred an additional 10 minutes. The layers were separated and the organic layer was washed with 4 L of 25% aqueous HCl. The pH of the aqueous layer was, adjusted from 0.98 to 11.6 with 1.6 L of 50% aqueous sodium hydroxide. Diatomaceous earth (Celite®) (1 kg) and 7 L of ethyl acetate were added. The mixture was stirred for 15 minutes, filtered through diatomaceous earth (Celite®) and the cake was washed with about 1 L of ethyl acetate. The layers were separated, the aqueous layer washed twice with 2 L of ethyl acetate, and the organic layers were combined and dried with sodium sulfate. The drying agent was removed by filtration, the cake was washed with ethyl acetate, and the filtrate was vacuum concentrated to about 2 L volume. This solution was treated with 510 g of silica gel for 30 minutes at 20°–25° C., filtered, and the silica gel was washed twice with 2 L of ethyl acetate. The filtrate was vacuum concentrated to a yellow slurry and displaced with 1 L of isopropanol to a final volume of about 275 mL. The slurry was granulated at 0°–5° C. for 30 minutes, filtered, washed with cold isopropanol, and dried giving 83.8 g (74.8%) of crude material (Mp 122°–125° C). A portion (48.3 g) of this material was purified by chromatography to give 38.6 g of the title compound as a yellow solid. Mp 124°–128° C. Spectral data for this compound are identical to the data reported in step 1 of Example 4.

C. Cis-3-(2-methoxybenzylamino)-2-phenylpiperidine HCl salt 3-(2-Methoxybenzylamino)-2-phenylpyridine (34.5 gms 0.119 moles) was dissolved in 0.8 L of acetic acid in a 2 L Parr bottle. To this solution was added 7.3 grams (0.032 moles) of platinum oxide, after which the vessel containing the catalyst was rinsed with 0.2 L of acetic acid and the rinse was added to the bottle. The mixture was placed on a Parr apparatus and hydrogenated (20–60 p.s.i. $H_2$) for 9.5 hours. Additional platinum oxide (3.6 grams, 0.016 moles) was added, and the reaction was hydrogenated for an additional 13 hours within the same pressure range. Another gram (0.004 moles) of platinum oxide was added and the mixture was hydrogenated for 2 hours. The reaction mixture was diluted with 0.4 L of 2B ethanol, filtered through (Celite®) and vacuum concentrated to an oil. The oil was dissolved in 0.6 L of methylene chloride, and the pH was brought to 10 with the addition of 0.8 L of 1N NaOH. The layers were separated, and the aqueous layer washed with methylene chloride (2×0.2 L each). The organic layers were combined, dried with sodium sulfate, and concentrated to an oil. The oil was dissolved in 40 mL of 2B ethanol, and 60 mL of HCl saturated 2B ethanol were added. White solids precipitated, and the slurry was cooled to 0°–5° C. and stirred for 2 hours. The solids were isolated by filtration and vacuum dried at 45° C. for 12–18 hours to give 30.6 gms (69.6%) of the cis-piperidine HCl salt. Mp 223°–226° C. $^1$H NMR (DMSO) δ 1.8–1.85 (d, 1H), 2.1–2.4 (m, 3H), 3.18 (m, 1H), 3.4–3.6 (m, 5H), 3.7 (s, 3H), 3.8–3.9 (d, 1H), 4.05 (s, 1H), 6.9–7.0 (m, 2H), 7.3–7.4 (m, 2H), 7.45–7.55 (m, 3H), 7.75 (d, 2H).

EXAMPLE 2

Cis-3-(2-methoxy-5-trifluoromethoxybenzylamino)-2-phenylpiperidine hydrochloride A. 2-Chloro-3-(2-methoxy-5-trifluoromethoxy benzylamino) pyridine To a 75 mL 3-necked round bottom flask fitted with mechanical stirrer, thermometer, addition funnel, and nitrogen inlet, were charged 29 mL acetic acid and 1.45 grams (11.3 mmoles) 3-amino-2-chloropyridine. The mixture was agitated for 5 minutes at 25° C. for dissolution. To the resulting solution was added 3.10 grams (14.1 mmoles/1.25 equivalents) of 2-methoxy-5-trifluoromethoxy benzaldehyde. Sodium triacetoxyborohydride, (4.79 grams, 22.6 mmoles, 2.0 equivalents) was added in portions while maintaining the temperature below 25° C. The reaction mixture was stirred 22 hours at 25° C. before adding another 0.5 grams of sodium triacetoxyborohydride. After stirring an additional 1 hour and 15 minutes, the reaction mixture was vacuum concentrated to 12.5 mL and partitioned between 26 mL each of methylene chloride and water. The pH was adjusted to 9.5 with 25% sodium hydroxide solution while maintaining a temperature of 25°–30° C. with cooling. The layers were separated, and the aqueous layer was washed with 14.5 mL methylene chloride. The methylene chloride layers were combined and dried with magnesium sulfate.

The magnesium sulfate was removed by filtration, and the methylene chloride filtrate was evaporated and displaced with ethyl acetate, which resulted in a yellow oil (3.49 gms/92.8% weight yield). The structure of the product was established by high resolution NMR and GC/MS. $^1$H NMR (CDCl$_3$) 7.70 (dd, 1H), 7.09 (bs, 1H), 7.02 (m, 2H), 6.85 (m, 2H), 4.95 (t, 1H), 4.36 (d, 2H), 3.88 (s, 3H).

B. 3-(2-methoxy-5-trifluoromethoxybenzylamino)-2-phenylpyridine

To a 250 mL 3 neck round bottom flask equipped with a mechanical stirrer, thermometer, addition funnel, and nitrogen inlet, were charged 98.1 mL of tetrahydrofuran, 3.27 grams (9.83 mmoles) of the 2-chloro-3-(2-methoxy-5-trifluoromethoxybenzylamino) pyridine and 1.93 grams (2.95 mmoles) of bis(triphenylphosphino)nickel(II) chloride. The black reaction mixture was stirred at 25 degree celsius for 40 minutes. Phenylmagnesium bromide (1M/THF, 38.4 mL, 38.4 mmoles) was added over a 25 minute period and the resulting black slurry was stirred for 2 hours at 25 degree celsius. During this time, the reaction was monitored by thin layer chromatography assay. The reaction mixture was cooled to 4° C., and quenched with 5.89 mL acetic acid. The reaction mixture was vacuum concentrated to a low volume and partitioned between 100 mL each of toluene and water. The organic layer was washed several times with water and concentrated to an oil. The oil was purifid by column chromatography to yield 1.88 grams (51.1%) of the desired material (as an oil). The structure of this compound was assigned on the basis of high resolution NMR. $^1$H NMR (CDCl$_3$) 8.05 (d, 1H), 7.63 (d, 2H), 7.45 (m, 3H), 7.12 (bs, 1H), 7.08 (m, 2H), 6.93 (dd, 1H), 6.85 (d, 1H), 4.71 (t, 1H), 4.26 (d, 2H), 3.78 (s, 3H).

C. Cis-3-(2-methoxy-5-trifluoromethoxybenzylamino)-2-phenylpiperidine hydrochloride To a 250 mL Parr bottle were charged 5.1 gms 5% Pt/C, 85 mL 1.0M HCl/CH$_3$OH, and 1.7 grams of 3-(2-methoxy-5-trifluoromethoxybenzylamino)-2-phenylpyridine. The reaction mixture was hydrogenated at 46–50 psi hydrogen at ambient temperature for 9.5 hours. After filtering the reaction mixture over Celite® and washing the cake with methanol, the filtrate was concentrated to a white solid. This material was repulped in acetonitrile at ambient temperature, filtered, and dried to yield 0.52 grams (25.2%) of a white material. The identity of this material was establishd by high resolution NMR.

EXAMPLE 3

(+)-Cis-3-(2-methoxybenzylamino)-2-phenylpiperidine hydrochloride salt

In a round bottom flask were placed 7.6 g of (+)-cis-3-(2-methoxybenzylamino)-2-phenylpiperidine and 30 mL of methanol. To this solution was added 3.9 g (100 mol %) of (R)-(−)-mandelic acid in 30 mL of methanol. The mixture was concentrated with a rotary evaporator, and the residue was triturated with ca. 200 mL of ether. The resulting white solid (10.4 g) was collected by suction filtration. A portion (4 g) of this solid was recrystallized from 384 mL of isopropyl alcohol. The stirring mixture was allowed to cool to room temperature overnight, and the resulting solid was collected by suction filtration and rinsed with 100 mL of ether to obtain 2.0 g of white solid, $[\alpha]_D$=+6.6°, (MeOH, c=0.48). A portion of this solid (1.9 g) was recrystallized from 400 mL of isopropanol, and the stirring mixture was allowed to cool to room temperature overnight. The resulting solid was collected by suction filtration and rinsed with 80 mL of ether to obtain 1.6 g of white solid, $[\alpha]_D$=+7.4°, (MeOH, c=0.50). A portion of this material (1.5 g) was partitioned between 150 mL of dichloromethane and 150 m of 1M aqueous sodium hydroxide, the layers were separated and the aqueous phase was extracted with 50 mL of dichloromethane. The combined organic fractions were dried ($Na_2SO_4$) and concentrated with a rotary evaporator to obtain 1.0 g of (+)-cis-3-(2-methoxybenzylamino)-2-phenylpiperidine as a clear oil. This oil was dissolved in 5 mL of $CH_2Cl_2$. To this solution was added HCl-saturated ether. The resulting mixture was filtered to afford 1.2 g of enantiomerically homogeneous(+)-cis-3-(2-methoxybenzylamino)-2-phenylpiperidine hydrochloride as a white solid, $[\alpha]_D$=+79.5° (MeOH, c=0.98).

EXAMPLE 4

Cis-3-(2-Methoxybenzylamino)-2-phenylpiperidine

1. Under a nitrogen atmosphere, in a round-bottom flask were placed 500 mg (2.9 mmol) of 2-phenyl-3-aminopyridine, 10 mL of methanol and 1 g of 3A molecular sieves. The pH of the system was adjusted to ca. 4.5, using methanol saturated with HCl, and 190 mg (2.9 mmol) of sodium cyanoborohydride was added to the system. The pH of the system was adjusted to 4.5, 474 mg (3.5 mmol) of 2-methoxybenzaldehyde was added and the mixture was stirred at room temperature overnight. The mixture was filtered through (Celite®) and the filtrate was concentrated. The residue was partitioned between $CH_2Cl_2$ and saturated aqueous sodium bicarbonate, the layers were separated and the aqueous phase was extracted with three portions of $CH_2Cl_2$. The combined organic fractions were dried ($Na_2SO_4$) and concentrated with a rotary evaporator. The crude material was purified by flash column chromatography to obtain 475 mg of 3-(2-methoxybenzylamino)-2-phenylpyridine. Mp. 128°–129° C.

$^1$H NMR (CDCl$_3$) δ 7.60 (d, 1H, J=6 Hz), 7.57 (d, 2H, J=6 Hz), 7.42 (t, 2H, J=6 Hz), 7.42 (t, 2H, J=6 Hz), 7.32 (m, 1H), 7.19 (m, 2H), 7.00 (m, 1H), 6.92 (d, 1H, J=7 Hz), 6.83 (m, 2H), 4.26 (d, 2H, J=6 Hz), 3.75 (s, 3H). Mass spectrum m/z 290 (parent). Calcd. for $C_{19}H_{18}N_2O$.1.85 HCl: C, 63.76; H, 5.58; N, 7.83. Found: C, 63.63; H, 5.38; N, 7.50.

2. 3-(2-Methoxybenzylamino)-2-phenylpyridine (25 mg) was dissolved in 3 mL of acetic acid. To this solution was added 3 mg of platinum oxide and the mixture was placed on a Parr apparatus (35–40 p.s.i. $H_2$) for ca. 2.5 hours. During this period, three additional 2.5 mg portions of catalyst were added to the system. The mixture was filtered through Celite® which had been rinsed well with ethanol and the filtrate was concentrated with a rotary evaporator. The residue was partitioned between $CH_2Cl_2$ and saturated aqueous sodium bicarbonate, the layers were separated and the aqueous phase was extracted with three portions of $CH_2Cl_2$. The combined organic fractions were dried ($Na_2SO_4$) and concentrated to afford 15 mg of the title compound contaminated with a trace of 3-(2-methoxybenzylamino)-2-phenylpyridine and a trace of material in which the 2-phenyl substituent had been reduced to a cyclohexyl moiety. The material prepared in this manner has spectral properties identical to those of the free base of the title compound of Example 1C.

EXAMPLE 5

(+)-Cis-3-(2-methoxybenzylamino)-2-phenylpiperidine HCl salt

A 22 L three neck round bottom flask was fitted with a mechanical stirrer, thermometer, and addition funnel. Methylene chloride (5.8 L) and 125.5 g (0.326 moles) (+)-cis-3-(2-methoxybenzylamino)-2-phenylpiperidine hydrochloride salt were added and the mixture was stirred for 15 minutes at 20°–25° C. Aqueous sodium hydroxide (2 L, 1N) was added over a 30 minute period, and the reaction mixture was stirred an additional 30 minutes, resulting in a pH of 12.25. The layers were separated, the aqueous layer washed twice with 2 L of methylene chloride, and the organic layers were combined and washed with 4 L of water. The organic layer was dried with 150 g of sodium sulfate for 30 minutes, and the drying agent was removed by filtration and washed with methylene chloride. The filtrate was concentrated atmospherically and displaced with 1 L of isopropanol to give about 90 g of an oil (93.3%). The oil free base was dissolved in 12.6 L of isopropanol and 47.1 g (0.310 moles) of (R)-(−)-mandelic acid was added, giving a pale yellow solution upon agitation. The solution was heated to reflux and concentrated to a volume of 5.5 L, giving a white slurry. The slurry was heated to 80° C. and then allowed to slowly cool and granulate over 12–18 hours. The reaction mixture was filtered, and the white solids were washed with 100 mL isopropyl ether and vacuum dried at 50° C. for 3 hours. The weight of the isolated mandelate salt was 57.4 g (84.3%) and the melting point was 180°–187° C. The filtrate was vacuum concentrated to 1 L, and the resulting solids (0.6 g) were isolated by filtration. The specific rotations of the first and second crops were +5.63° (MeOH, c=0.64) and +5.65° (MeOH, c=0.76), respectively.

A 12 L three neck round bottom flask was equipped with a mechanical stirrer, condenser, and thermometer. Filtered isopropanol (5.6 L) and 58 g of the mandelate salt were added and the mixture was heated to reflux (about 80° C.) for 30 minutes. The reaction mixture was allowed to slowly cool and solids began precipitating at 50° C. After stirring 5 hours, the temperature was 20°–25° C. The solids were then isolated by filtration, and washed with isopropanol and isopropyl ether. The solids were vacuum dried for 12–18 hours at 50° C. giving 54.7 g of material. The specific rotation of this material was +6.82° (MeOH, c=0.60). The isolated material (52.7 g) was again recrystallized using the same procedure. Fifty grams of dried solids were isolated and the specific rotation was +6.7° (MeOH, c=0.78).

A 12 L three neck round bottom flask was fitted with a mechanical stirrer. To the system were added 4.9 L methylene chloride, 49.3 g of the mandelate salt, 4.9 L of 1N aqueous sodium hydroxide, and the mixture was stirred for 15 minutes at 20°–25° C. The layers were separated and the aqueous layer was washed twice with 750 mL methylene chloride. These extracts were combined with the organic layers, and washed with 2 L water. The organic layer was dried with sodium sulfate, concentrated atmospherically and displaced with 2B ethanol to an oil. Two hundred twenty milliliters of 2B ethanol was treated with 32 g of HCl gas, and 150 mL of the resulting solution was added to the oil dissolved in 220 mL of 2B ethanol. White solids precipitated and the slurry was stirred at 20°–25° C. for 1 hour and for 2 hours at 0°–5° C. The solids were isolated by filtration, washed with 2B ethanol, and dried at 45°–50° C. for 12–18 hours giving 39.4 g of material. The specific rotation of this material was +79.63° (MeOH, c=0.70), and the melting point was 267°–268° C. The resolution yield for the enantiomer was 62.9%.

EXAMPLE 6

3-(2-Methoxybenzylamino)2-phenylpyridine

The mother liquor from the R-mandelic acid resolution of cis-3-(2-methoxybenzylamino)-2-phenylpiperidine (85 g)

was partitioned between 1.5 L of methylene chloride and 1.5 L of 1N aqueous sodium hydroxide. The layers were separated, and the aqueous layer was washed twice with 0.5 L of methylene chloride. The organic layers were combined, dried with magnesium sulfate, filtered, and the magnesium sulfate cake was washed with methylene chloride. The filtrate was concentrated atmospherically to an oil, and then pumped under vacuum giving 50 g of oil. This material was combined with 0.5 L of xylenes and 50 g of 10% Pd/C (50% water wet), and heated to reflux (106° C.). The reaction mixture was heated at reflux for 3.5 hours, cooled to 20°–25° C., and filtered through diatomaceous earth (Celite®) the cake was washed with the xylene, and the filtrate was vacuum concentrated to 39.6 g of an oil. Thin layer chromatography showed that the oil contained two major components, one with the same Rf (distance traveled by solute divided by distance traveled by mobile phase) as that of the desired product. The entire batch was then purified by chromatography to isolate the desired material (400 g of 63–200 micron silica gel, eluant: 3 parts hexanes/1 part ethyl acetate). The eluant was collected in 0.5 L fractions, and the desired material was collected in fractions 5–9. The combined fractions were vacuum concentrated to a yellow solid (6.5 g). This material was repulped with 25 mL of cold isopropanol, filtered, washed with cold isopropanol, and dried to give 4.5 g of desired material. M.p. 123°–127° C. This material had spectral properties that were identical to those of the title compound of Example 4, part 1.

EXAMPLE 7

3-Amino-2-phenylpyridine

Under a nitrogen atmosphere, in a three-neck round-bottom flask equipped with a pressure-equalizing addition funnel and a thermometer were placed 12.2 g (94.9 mmol) of 3-amino-2-chloropyridine and 1.05 L of THF. To the system were added 25.0 g (47.3 mmol) of [1,2-bis-(diphenylphosphino)ethane]nickel (II) chloride, and the orange slurry was stirred at room temperature for 0.5 hours. To the system were added dropwise 40 mL (120 mmol) of 3M phenylmagnesium bromide in ether (temperature of reaction mixture rose to 35° C.), and the mixture was stirred for 2 days. During this period, additional (100 mL) 3M phenylmagnesium bromide was added to the system. The reaction mixture was cooled in an ice bath, 300 mL of 1M aqueous HCl was added to the system, the layers were separated and the organic phase was extracted with 1M aqueous HCl. The HCl extracts were washed with three portions of ethyl acetate and made basic with solid NaOH. The basic solution was stirred with ethyl acetate and Celite (trademark) for 0.5 hours. The mixture was filtered, the solids were rinsed with ethyl acetate and the filtrate layers were separated. The aqueous layer was extracted with ethyl acetate and the ethyl acetate fractions were washed with brine, dried ($Na_2SO_4$) and concentrated (rotary evaporator) to obtain 11.4 g of brown oil. The crude material was purified by flash column chromatography on silica gel using 4:1 hexanes/ethyl acetate as the eluant to obtain 7.7 g (48% yield) of the title compound as a solid; mp 59°–62° C.; [lit: 62°–64° C. Can. J, Chem. 38, 2152 (1960)]. Anal. Calc'd for $C_{11}H_{10}N_2$: C, 77.62; H, 5.92; N, 16.46. Found: C, 77.30; H, 5.99; N, 16.57.

EXAMPLE 8

3-(2-Methoxybenzylamino)-2-phenylpyridine

To a 22 L 3 neck round bottom flask equipped with a mechanical stirrer, thermometer, addition funnel, and nitrogen inlet were charged 6.3 L tetrahydrofuran (THF), 103 grams (0.16 moles) bis(triphenylphosphine)nickel (II) chloride, and 157 grams (0.63 moles) 2-chloro-3-(2-methoxybenzylamino)pyridine. The orange slurry was stirred at 25° C. for 30 minutes. A total of 555 mL (1.7 moles) phenylmagnesium bromide was added over a 4.5 hour period, and the resulting black slurry was stirred for 17.5 hours at 25° C. The reaction mixture was cooled to 18° C., and 190 mL acetic acid was slowly charged over a 45 minute period. The reaction mixture was cooled to 8° C. and granulated at this temperature for 2.5 hours. The dark slurry was filtered and the wet material dried giving 182 grams (100%) of crude product.

Crude 3-(2-methoxybenzylamino)-2-phenylpyridine (182 grams) was partitioned between 2.7 L toluene and 2.7 L water. The pH of the medium was 2.1 and was adjusted to pH 12.0 with 60 mL 25% NaOH. The biphasic mixture was filtered through Celite (trademark) and the cake washed with toluene. The layers were separated, the aqueous layer was washed with 910 mL of toluene, and the organic layers were combined and backwashed with 1 L water. The toluene layer was treated with 25 grams each KBB Darco (trademark) and magnesium sulfate for 30 minutes and filtered through Celite®, and the cake was washed with toluene. The filtrate was vacuum concentrated to a volume of approximately 200 mL and then displaced with 200 mL isopropanol. After stirring 12–18 hours at 20°–25° C., the yellow slurry was cooled to 5° C., granulated for 30 minutes, filtered, washed with cold isopropanol, and air dried to give 92 grams of 3-(2-methoxybenzylamino)-2-phenylpyridine: mp 126°–129° C. The overall reaction and purification yield was 50.3%. The material obtained exhibited spectral properties identical to those reported in step 1 of Example 3.

EXAMPLE 9

R-Mandelic Acid Salt of (2S,3S)-3-(2-Methoxybenzylamino)-2-phenylpiperidine

To a 2.5 L Parr bottle was charged 75 grams 5% Pt/C, 625 mL of 1.5M methanolic hydrogen chloride, and a solution of 25 grams (0.09 moles) 3-(2-methoxybenzylamino)-2-phenylpyridine in 625 mL 1.5M methanolichydrogen chloride. The system was purged three times with nitrogen and placed under an atmosphere of hydrogen (30–60 psi) for 6.5 hours. The reaction mixture was filtered through Celite® and the cake was washed with 600 mn methanol/water and held as a solution at 20°–25° C. for 12–16 hours. The solution was vacuum concentrated to 300 mL and added to 750 mL of methylene chloride. The pH of the mixture was adjusted to 10 with 200 mL of 25% NaOH. The layers were separated, the aqueous layer was washed with 250 mL methylene chloride and the organic layers were combined and dried with magnesium sulfate for 30 minutes. After filtering off the drying agent, the methylene chloride filtrate was atmospherically concentrated to an oil and displaced with isopropanol. The oil was dissolved in 718 mL isopropanol, charged with 9.5 grams (0.06 moles) R-mandelic acid, and stirred for 12–18 hours at 20°–25° C. The white solids were isolated via filtration and dried, giving 8.8 grams (45.5%) of mandelate salt. The specific rotation for this material was $[\alpha]_D = 1.93°$ ($CH_3OH$, c=0.76). The crude material (8.6 grams) was purified by recrystallization. After combining with 654 mL of isopropanol, the mixture was heated to reflux, cooled to 20°–25° C., stirred 2 hours at that temperature, filtered, and dried 12–18 hours at 40° C. to give 7.7 grams (89.5%) of recrystallized material. The specific rotation was +5.50° (C=0.7, MeOH). $^1$H NMR (DMSO/CD$_3$OD) δ 1.5–1.75 (m, 2H), 1.9–2.1 (m, 2H), 2.85 (s, 1H), 2.95 (t, 1H), 3.25 (s, 1H), 3.3 (d, 1H), 3.4 (s, 3H), 3.55 (d, 1H), 4.15 (s, 4H), 4.3 (s, 1H), 4.55 (s, 1H), 6.8–6.9 (m, 2H), 7.0–7.1 (d, 1H), 7.15–7.25 (m, 4H), 7.3–7.5 (m, 7H).

EXAMPLE 10

Cis-3-(3-fluoro-4-methoxybenzylamino)-2-phenylpiperidine

The title compound was prepared according to the procedure of Example 1, replacing 2-methoxybenzaldehyde in step A with 3-fluoro-4-methoxybenzaldehyde. M.p. 272°–274° C. (HCl salt). $^1$H NMR (CDCl$_3$) δ 1.34–2.04 (m, 4H), 2.68–2.82 (m, 2H), 3.12–3.26 (m, 1H), 3.22 (d, 1H, J=12), 3.40 (d, 1H, J=12), 3.82 (s, 3H), 3.85 (d, 1H, J=4), 6.60–6.76 (m, 3H), 7.10–7.32 (m, 5H). HRMS Calc'd for C$_{19}$H$_{23}$FN$_2$O: 314.1791. Found: 314.1773. Anal. Calc'd for C$_{19}$H$_{23}$FN$_2$O.2HCl.1.1H$_2$O: C, 56.05; H, 6.73; N, 6.88. Found: C, 55.96; H, 6.48; N, 6.71.

EXAMPLE 11

Cis-3-(2,5-dimethoxybenzylamino)-2-phenylpiperidine

The title compound was prepared according to the procedure of Example 1, replacing 2-methoxybenzaldehyde in step A with 2,5-dimethoxybenzaldehyde. M.p. 252°–254° C. (HCl salt). $^1$H NMR (CDCl$_3$) δ 1.28–1.40 (m, 1H), 1.48–1.92 (m, 2H), 2.02–2.14 (m, 1H), 2.66–2.80 (m, 2H), 3.14–3.24 (m, 1H), 3.32 (d, 1H, J=18), 3.38 (s, 3H), 3.56 (d, 1H, J=18), 3.66 (s, 3H), 3.83 (d, 1H, J=3), 6.48–6.62 (m, 3H), 7.10–7.26 (m, 5H). HRMS Calc'd for C$_{20}$H$_{26}$N$_2$O$_2$: 326.1995. Found: 326.1959. Anal. Calc'd for C$_{20}$H$_{26}$N$_2$O$_2$.2HCl.0.3H$_2$O: C, 59.34; H, 7.12; N, 6.92. Found: C, 59.33; H, 6.96; N, 6.76.

EXAMPLE 12

Cis-3-(2-methoxy-5-methylbenzylamino)-2-phenylpiperidine

The title compound was prepared according to the procedure of Example 4, replacing 2-methoxybenzaldehyde with 2-methoxy-5-methylbenzaldehyde. M.p. 245°–247° C. (HCl salt). $^1$H NMR (CDCl$_3$) δ 1.30–1.42 (m, 1H), 1.48–1.98 (m, 2H), 2.04–2.16 (m, 1H), 2.18 (s, 3H), 2.68–2.70 (m, 2H), 3.18–3.30 (m, 1H), 3.35 (d, 1H, J=12), 3.40 (s, 3H), 3.58 (d, 1H, J=12), 3.85 (d, 1H, J=3), 6.53 (d, 1H, J=8), 6.71 (d, 1H, J=2), 6.88 (dd, 1H, J=4, 10), 7.14–7.26 (m, 5H). HRMS Calc'd for C$_{20}$H$_{26}$N$_2$O: 310.2041. Found: 310.2024. Anal. Calc'd for C$_{20}$H$_{26}$N$_2$O.2HCl.1.2H$_2$O: C, 59.31; H, 7.56; N, 6.92. Found: C, 59.31; H, 7.40; N, 6.85.

EXAMPLE 13

Cis-3-(3-methoxybenzylamino)-2-phenylpiperidine

The title compound was prepared according to the procedure of Example 4, replacing 2-methoxybenzaldehyde with 3-methoxybenzaldehyde. M.p. 243°–246° C. (HCl salt). $^1$H NMR (CDCl$_3$) δ 1.32–1.42 (m, 1H), 1.48–1.90 (m, 2H), 1.96–2.04 (m, 1H), 2.68–2.78 (m, 1H), 2.85 (d, 1H, J=4), 3.16–3.26 (m, 1H), 3.29 (d, 1H, J=12), 3.46 (d, 1H, J=12), 3.68 (s, 3H), 3.85 (d, 1H, J=3), 6.50–6.58 (m, 2H), 6.62–6.68 (m, 1H), 7.04 (t, 1H, J=8), 7.16–7.38 (m, 5H). HRMS Calc'd for C$_{19}$H$_{24}$N$_2$O: 296.1885. Found: 296.1873.

Anal. Calc'd for C$_{19}$H$_{24}$N$_2$O.2HCl.0.3H$_2$O: C, 60.89; H, 6.75; N, 7.48. Found: C, 60.72; H, 6.84; N, 7.27.

EXAMPLE 14

S-(+)-Mandelic Acid Salt of (2S,3S)-3-(2-methoxy-5-trifluoromethoxybenzyl)amino-2-phenylpiperidine To 210 mg (0.55 mmol) of cis-3-(2-methoxy-5-trifluoromethoxybenzyl)amino-2-phenylpiperidine, dissolved in 20 mL isopropyl ether, was added 83.9 mg (0.55 mmol) of S-(+)-mandelic acid. The mixture was heated to reflux to dissolve all of the acid. After 5 minutes the mixture became cloudy and another 12 mL of isopropyl ether was added. The mixture was stirred at reflux for another 10 minutes, then cooled to room temperature and stirred for 3 hours. The white solid was collected by vacuum filtration and air-dried to provide 112.3 mg (76.4% theoretical yield) of the desired salt, m.p. 145°–147° C.

$[\alpha]D^{25}=+57.7°$, c=0.66, MeOH.

An 80 mg portion of the mandelate salt was dissolved in 15 mL of dichloromethane and was washed with 10% aqueous sodium hydroxide solution. The organic layer was separated, dried over magnesium sulfate, filtered and concentrated in vacuo. After drying under high vacuum, 53 mg (92.8%) of (2S,3S)-3-(2-methoxy-5-trifluoromethoxybenzyl)amino-2-phenylpiperidine was obtained as an oil.

$[\alpha]D^{25}=+49.9°$ c=1.01, CHCl$_3$.

To prepare the hydrochloride salt, 40 mg of the resolved amine was dissolved in 10 mL of diethyl ether and hydrogen chloride gas was bubbled into the solution. After stirring for 20 minutes, the white solid was collected by filtration, washed with diethyl ether and air-dried to provide 36 mg (73% yield) of (2S,3S)-3-(2-methoxy-5-trifluoromethoxybenzyl)amino-2-phenylpiperidine hydrochloride, m.p. 251°–255° C.

$[\alpha]D^{25}=+67.2°$, c=0.97, MeOH.

We claim:

1. A process for preparing a compound of the formula

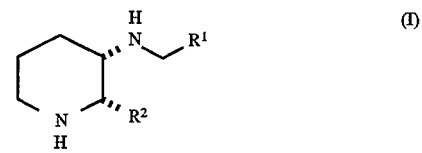

(I)

wherein R$^1$ is aryl selected from indanyl, phenyl and naphthyl; heteroaryl selected from thienyl, furyl, pyridyl and quinolyl; and cycloalkyl having 3–7 carbon atoms, wherein one of said carbon atoms may optionally be replaced by nitrogen oxygen or sulfur; wherein each of said aryl and heteroaryl groups may optionally be substituted with one or more substituents, and said (C$_3$–C$_7$) cycloalkyl may optionally be substituted with one or two substituents, said substituents being independently selected from halo, nitro, amino, cyano, phenyl, hydroxyl, (C$_1$–C$_6$) alkylamino, (C$_1$–C$_6$) dialkylamino,

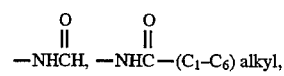

(C$_1$–C$_{10}$) alkoxy optionally substituted with from one to three fluorine atoms and (C$_1$–C$_{10}$) alkyl optionally substituted with from one to three fluorine atoms, wherein the nitrogen atoms of said amino and (C$_1$–C$_6$) alkylamino groups may optionally be protected with an appropriate amino protecting group; and $R^2$ is thienyl, benzhydryl, naphthyl or phenyl substituted with from one to three substituents independently selected from chloro, bromo, fluoro, iodo, $(C_1-C_{10})$ alkoxy optionally substituted with from one to three fluorine atoms and $(C_1-C_{10})$ alkyl optionally substituted with from one to three fluorine atoms, comprising: (a) reacting a compound of the formula

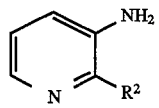 (IV)

wherein $R^2$ is defined as above, with either (i) a compound of the

wherein $R^1$ is defined as above and X is a leaving group selected from the group consisting of chloro, bromo, iodo, mesylate or tosylate, followed by treatment of the resulting amide with a reducing agent, (ii) a compound of the formula $R^1CHO$, wherein $R^1$ is defined as above, in the presence of a reducing agent, or (iii) a compound of the formula $R^1CH_2X$, wherein $R^1$ is defined as above and X is a leaving group, to produce a compound of the formula

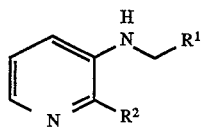 (II)

wherein $R^1$ and $R^2$ are defined as above; and (b) reducing said compound of formula II.

2. A process according to claim 1, wherein said compound of the formula IV is reacted with said compound of the formula $R^1CHO$ in the presence of a reducing agent.

3. A process according to claim 2, wherein said reducing agent is sodium triacetoxyborohydride.

4. A process according to claim 2, wherein said reducing agent is sodium cyanoborohydride.

5. A process according to claim 2, wherein said reaction is conducted in a lower alcohol solvent selected from the group consisting of methanol, ethanol, propanol and butanol, at a temperature from about $-60°$ C. to about $50°$ C.

6. A process according to claim 2, wherein said reaction is conducted in acetic acid at a temperature from about $-60°$ C. to about $50°$ C.

7. A process according to claim 1, wherein said compound of formula I formed thereby is a compound wherein $R^1$ and $R^2$ are the same or different and each of $R^1$ and $R^2$ is phenyl optionally substituted with one to three substituents independently selected from chlorine, fluorine, $(C_1-C_{10})$alkyl optionally substituted with from one to three fluorine atoms and $(C_1-C_{10})$alkoxy optionally substituted with from one to three fluorine atoms.

8. A process according to claim 1, wherein said compound of formula I formed thereby is a compound wherein $R^1$ is 2-methoxyphenyl and $R^2$ is phenyl.

9. A process according to claim 1, wherein said compound of formula I formed thereby is a compound wherein $R^1$ is 5-trifluoromethoxy-2-methoxyphenyl and $R^2$ is phenyl.

10. A process according to claim 1, wherein said compound of formula I formed thereby is a compound wherein $R^1$ is 3-fluoro-4-methoxyphenyl and $R^2$ is phenyl.

11. A process according to claim 1, wherein said compound of formula I formed thereby is a compound wherein $R^1$ is 2,5-dimethoxyphenyl and $R^2$ is phenyl.

12. A process according to claim 1, wherein said compound of formula I formed thereby is a compound wherein $R^1$ is 2-methoxy-5-methylphenyl and $R^2$ is phenyl.

13. A process for preparing a compound of the formula

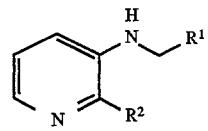 (II)

wherein $R^1$ is aryl selected from indanyl, phenyl and naphthyl; heteroaryl selected from thienyl, furyl, pyridyl and quinolyl; and cycloalkyl having 3–7 carbon atoms, wherein one of said carbon atoms may optionally be replaced by nitrogen oxygen or sulfur; wherein each of said aryl and heteroaryl groups may optionally be substituted with one or more substituents, and said $(C_3-C_7)$ cycloalkyl may optionally be substituted with one or two substituents, said substituents being independently selected from halo, nitro, amino, cyano, phenyl, hydroxyl, $(C_1-C_6)$ alkylamino, $(C_1-C_6)$ dialkylamino,

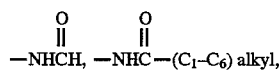

$(C_1-C_{10})$ alkoxy optionally substituted with from one to three fluorine atoms and $(C_1-C_{10})$ alkyl optionally substituted with from one to three fluorine atoms, wherein the nitrogen atoms of said amino and $(C_1-C_6)$ alkylamino groups may optionally be protected with an appropriate amino protecting group; and $R^2$ is thienyl, benzhydryl, naphthyl or phenyl optionally substituted with from one to three substituents independently selected from chloro, bromo, fluoro, iodo, $(C_1-C_{10})$ alkoxy optionally substituted with from one to three fluorine atoms and $(C_1-C_{10})$ alkyl optionally substituted with from one to three fluorine atoms;

comprising reacting a compound of the formula

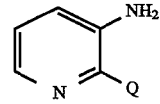 (V)

wherein Q is hydrogen, chloro, fluoro, bromo or iodo, with either (i) a compound of the formula

wherein $R^1$ is defined as above and X is a leaving group, followed by treatment of the resulting amide with a reducing agent, (ii) a compound of the formula $R^1CHO$, wherein $R^1$ is defined as above, in the presence of a reducing agent, or (iii) a compound of the formula $R^1CH_2X$, wherein $R^1$ is defined as above and X is a leaving group selected from the group consisting of chloro, bromo, iodo, mesylate or tosylate, to produce a compound of the formula

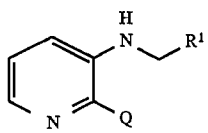

wherein $R^1$ and Q are defined as above, and then reacting said compound of formula III with $(R^2)$-halogen wherein $R^2$ is defined as above and halogen represents chlorine, fluorine, bromine or iodine, in the presence of a transition metal catalyst, or with an $(R^2)$-containing organometallic compound, wherein $R^2$ is defined as above.

14. A process according to claim 13, wherein said $(R^2)$-containing organometallic compound is $(R^2)$-magnesium bromide or $(R^2)$-lithium.

15. A process according to claim 13, wherein said compound of the formula II formed thereby is reduced to produce the corresponding compound of the formula

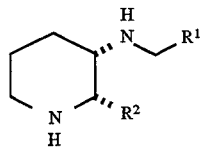

wherein $R^1$ is aryl selected from indanyl, phenyl and naphthyl; heteroaryl selected from thienyl, furyl, pyridyl and quinolyl; and cycloalkyl having 3–7 carbon atoms, wherein one of said carbon atoms may optionally be replaced by nitrogen, oxygen or sulfur; wherein each of said aryl and heteroaryl groups may optionally be substituted with one or more substituents, and said ($C_3$–$C_7$) cycloalkyl may optionally be substituted with one or two substituents, said substituents being independently selected from halo, nitro, amino, cyano, phenyl, hydroxyl, ($C_1$–$C_6$) alkylamino, ($C_1$–$C_6$) dialkylamino,

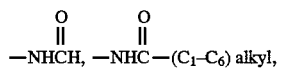

($C_1$–$C_{10}$) alkoxy optionally substituted with from one to three fluorine atoms and ($C_1$–$C_{10}$) alkyl optionally substituted with from one to three fluorine atoms, wherein the nitrogen atoms of said amino and ($C_1$–$C_6$) alkylamino groups may optionally be protected with an appropriate protecting group; and $R^2$ is thienyl, benzhydryl, naphthyl or phenyl optionally substituted with from one to three substituents independently selected from chloro, bromo, fluoro, iodo, ($C_1$–$C_{10}$) alkoxy optionally substituted with from one to three fluorine atoms and ($C_1$–$C_{10}$) alkyl optionally substituted with from one to three fluorine atoms.

16. A process according to claim 14, wherein said $(R^2)$-magnesium bromide is phenylmagnesium bromide.

17. A process according to claim 13, wherein said compound of formula II formed thereby is a compound wherein $R^1$ and $R^2$ are the same or different and each of $R^1$ and $R^2$ is phenyl optionally substituted with one to three substituents independently selected from chlorine, fluorine, ($C_1$–$C_{10}$) alkyl optionally substituted with from one to three fluorine atoms and ($C_1$–$C_{10}$) alkoxy optionally substituted with from one to three fluorine atoms.

18. A process according to claim 13, wherein said compound of formula II formed thereby is a compound wherein $R^1$ is 2-methoxyphenyl and $R^2$ is phenyl.

19. A process according to claim 13, wherein said compound of formula II formed thereby is a compound wherein $R^1$ is 5-trifluoromethoxy-2-methoxyphenyl and $R^2$ is phenyl.

20. A process according to claim 13, wherein said compound of formula II formed thereby is a compound wherein $R^1$ is 3-fluoro-4-methoxyphenyl and $R^2$ is phenyl.

21. A process according to claim 13, wherein said compound of formula II formed thereby is a compound wherein $R^1$ is 2,5-dimethoxyphenyl and $R^2$ is phenyl.

22. A process according to claim 13, wherein said compound of formula II formed thereby is a compound wherein $R^1$ is 2-methoxy-5-methylphenyl and $R^2$ is phenyl.

23. A process for preparing compounds of the formula

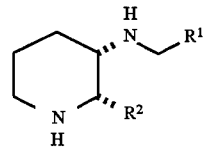

wherein $R^1$ is aryl selected from indanyl, phenyl and naphthyl; heteroaryl selected from thienyl, furyl, pyridyl and quinolyl; and cycloalkyl having 3–7 carbon atoms, wherein one of said carbon atoms may optionally be replaced by nitrogen oxygen or sulfur; wherein each of said aryl and heteroaryl groups may optionally be substituted with one or more substituents, and said ($C_3$–$C_7$) cycloalkyl may optionally be substituted with one or two substituents, said substituents being independently selected from halo, nitro, amino, cyano, phenyl, hydroxyl, ($C_1$–$C_6$) alkylamino, ($C_1$–$C_6$) dialkylamino,

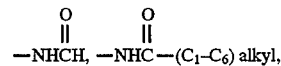

($C_1$–$C_{10}$) alkoxy optionally substituted with from one to three fluorine atoms and ($C_1$–$C_{10}$) alkyl optionally substituted with from one to three fluorine atoms, wherein the nitrogen atoms of said amino and ($C_1$–$C_6$) alkylamino groups may optionally be protected with an appropriate amino protecting group; and $R^2$ is thienyl, benzhydryl, naphthyl or phenyl optionally substituted with from one to three substituents independently selected from chloro, bromo, fluoro, iodo, ($C_1$–$C_{10}$) alkoxy optionally substituted with from one to three fluorine atoms and ($C_1$–$C_{10}$) alkyl optionally substituted with from one to three fluorine atoms;

comprising reacting a compound of the formula

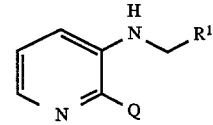

wherein $R^1$ is defined as above and Q is hydrogen, chloro, fluoro, bromo or iodo, with $(R^2)$-halogen wherein $R^2$ is defined as above and halogen represents chlorine, bromine, fluorine or iodine, wherein $R^2$ is defined as above, in the presence of a transition metal catalyst, or with an $(R^2)$-containing organometallic compound, to produce a compound of the formula

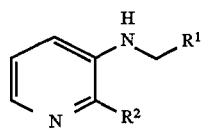

wherein $R^1$ and $R^2$ are defined as above, and then reducing the compound of formula II so formed.

24. A process according to claim 23, wherein said $R^2$-containing organometallic compound is $(R^2)$-magnesium bromide or $(R^2)$-lithium.

25. A process according to claim 23, wherein said compound of the formula III is obtained by reacting a compound of the formula

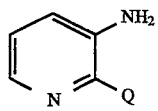

wherein Q is hydrogen, chloro, fluoro, bromo or iodo, with either (i) a compound of the formula

$$R^1CX$$

wherein $R^1$ is aryl selected from indanyl, phenyl and naphthyl; heteroaryl selected from thienyl, furyl, pyridyl and quinolyl; and cycloalkyl having 3–7 carbon atoms, wherein one of said carbon atoms may optionally be replaced by nitrogen, oxygen or sulfur; wherein each of said aryl and heteroaryl groups may optionally be substituted with one or more substituents, and said $(C_3-C_7)$ cycloalkyl may optionally be substituted with one or two substituents, said substituents being independently selected from halo, nitro, amino, cyano, phenyl, hydroxyl, $(C_1-C_6)$ alkylamino, $(C_1-C_6)$ dialkylamino,

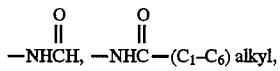

$(C_1-C_{10})$ alkoxy optionally substituted with from one to three fluorine atoms and $(C_1-C_{10})$ alkyl optionally substituted with from one to three fluorine atoms, wherein the nitrogen atoms of said amino and $(C_1-C_6)$ alkylamino groups may optionally be protected with an appropriate amino protecting group; and X is a leaving group selected from the group consisting of chloro, bromo, iodo, mesylate or tosylate, followed by treatment of the resulting amide with a reducing agent, (ii) a compound of the formula $R^1CHO$, wherein $R^1$ is defined as above, in the presence of a reducing agent, or (iii) a compound of the formula $R^1CH_2X$, wherein $R^1$ is defined as above and X is a leaving group.

26. A process according to claim 23, wherein the reaction of said compound of the formula III with said $(R^2)$-halogen or said $(R^2)$-containing organometallic compound is conducted in the presence of a nickel catalyst at a temperature from about 0° C. to about 60° C.

27. A process according to claim 26, wherein said nickel catalyst is [1,2-bis-(diphenylphosphino)ethane] nickel (II) chloride or bis (triphenylphosphine) nickel (II) chloride.

28. A process according to claim 26, wherein said reaction is conducted in tetrahydrofuran.

29. A process according to claim 23, wherein said compound of formula I formed thereby is a compound wherein $R^1$ and $R^2$ are the same or different and each of $R^1$ and $R^2$ is phenyl optionally substituted with one to three substituents optionally substituted with from one to three fluorine atoms independently selected from chlorine, fluorine, $(C_1-C_{10})$ alkyl optionally substituted with from one to three fluorine atoms and $(C_1-C_6)$ alkoxy optionally substituted with from one to three fluorine atoms.

30. A process according to claim 23, wherein said compound of formula I formed thereby is a compound wherein $R^1$ is 2-methoxyphenyl and $R^2$ is phenyl.

31. A process according to claim 23, wherein said compound of formula I formed thereby is a compound wherein $R^1$ is 5-trifluoromethoxy-2-methoxyphenyl and $R^2$ is phenyl.

32. A process according to claim 23, wherein said compound of formula I formed thereby is a compound wherein $R^1$ is 3-fluoro-4-methoxyphenyl and $R^2$ is phenyl.

33. A process according to claim 23, wherein said compound of formula I formed thereby is a compound wherein $R^1$ is 2,5-dimethoxyphenyl and $R^2$ is phenyl.

34. A process according to claim 23, wherein said compound of formula I formed thereby is a compound wherein $R^1$ is 2-methoxy-5-methylphenyl and $R^2$ is phenyl.

35. A process for preparing (+)-cis-3-(2-methoxybenzylamino)-2-phenylpiperidine, comprising reacting a racemic mixture of said compound with (R)-(−)-mandelic acid in a suitable organic reaction inert solvent, removing the solvent by filtration and treating the resulting salt with a base.

36. A process according to claim 35, wherein the reaction inert solvent is isopropanol.

37. A process according to claim 35, wherein the base is sodium hydroxide.

38. A process for preparing compounds of the formula

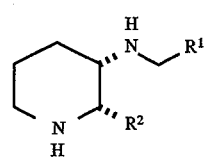

wherein $R^1$ is aryl selected from indanyl, phenyl and naphthyl; heteroaryl selected from thienyl, furyl, pyridyl and quinolyl; and cycloalkyl having 3–7 carbon atoms, wherein one of said carbon atoms may optionally be replaced by nitrogen oxygen or sulfur; wherein each of said aryl and heteroaryl groups may optionally be substituted with one or more substituents, and said $(C_1-C_7)$ cycloalkyl may optionally be substituted with one or two substituents, said substituents being independently selected from halo, nitro, amino, cyano, phenyl, hydroxyl, $(C_1-C_6)$ alkylamino, $(C_1-C_6)$ dialkylamino,

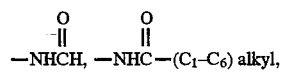

$(C_1-C_{10})$ alkoxy optionally substituted with from one to three fluorine atoms and $(C_1-C_{10})$ alkyl optionally substituted with from one to three fluorine atoms, wherein the nitrogen atoms of said amino and $(C_1-C_6)$ alkylamino groups may optionally be protected with an appropriate amino protecting group; and $R^2$ is thienyl, benzhydryl, naphthyl or phenyl substituted with from one to three substituents independently selected from chloro, bromo, fluoro, iodo, $(C_1-C_{10})$ alkoxy optionally substituted with from one to three fluorine atoms and $(C_1-C_{10})$ alkyl optionally substituted with from one to three fluorine atoms;

comprising reacting a compound of the formula

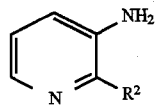

wherein $R^2$ is defined as above, with a compound of the formula $R^1CHO$, wherein $R^1$ is defined as above, in the presence of a drying agent or using an apparatus designed to remove azeotropically the water generated, to produce an imine of the formula

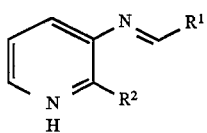

wherein $R^1$ and $R^2$ are defined as above, and then either reducing the imine with hydrogen to form a compound of the formula I, or reacting the imine with a reducing agent to form a compound of the formula

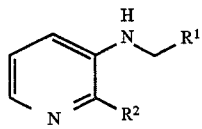

(II)

wherein $R^1$ and $R^2$ are defined as above, and then reacting said compound of the formula II with a reducing agent to form a compound of the formula I.

39. A process according to claim 38, wherein the reducing agent used to obtain the compound of formula II is sodium triacetoxyborohydride.

40. A process according to claim 38, wherein said compound formula I formed thereby is a compound wherein $R^1$ and $R^2$ are the same or different and each of $R^1$ and $R^2$ is phenyl optionally substituted with one to three substituents optionally substituted with from one to three fluorine atoms independently selected from chlorine, fluorine, ($C_1$–$C_{10}$) alkyl optionally substituted with from one to three fluorine atoms and ($C_1$–$C_{10}$) alkoxy optionally substituted with from one to three fluorine atoms.

41. A process according to claim 38, wherein said compound of formula I formed thereby is a compound wherein $R^1$ is 2-methoxyphenyl and $R^2$ is phenyl.

42. A process according to claim 38, wherein said compound of formula I formed thereby is a compound wherein $R^1$ is 5-trifluoromethoxy-2-methoxyphenyl and $R^2$ is phenyl.

43. A process according to claim 38, wherein said compound of formula I formed thereby is a compound wherein $R^1$ is 3-fluoro-4-methoxyphenyl and $R^2$ is phenyl.

44. A process according to 38, wherein said compound of formula I formed thereby is a compound wherein $R^1$ is 2,5-dimethoxyphenyl and $R^2$ is phenyl.

45. A process according to claim 38, wherein said compound of formula I formed thereby is a compound wherein $R^1$ is 2-methoxy-5-methylphenyl and $R^2$ is phenyl.

46. A process for preparing (+)-cis-3-(2-methoxy-5-trifluoromethoxybenzylamino)-2-phenylpiperidine, comprising reacting a racemic mixture of said compound with (S)-(+)-mandelic acid in a suitable organic reaction inert solvent, removing the solvent by filtration and treating the resulting salt with a base.

47. A process according to claim 46, wherein the reaction inert solvent is isopropyl ether.

48. A process according to claim 46, wherein the base is sodium hydroxide.

* * * * *